United States Patent
Black, Sr.

(10) Patent No.: US 9,498,491 B2
(45) Date of Patent: Nov. 22, 2016

(54) METHODS FOR EXTRACTION OF BIOACTIVE POLYELECTROLYTES FROM HUMIFIED ORGANIC MATERIALS

(75) Inventor: Gary W. Black, Sr., Pottstown, PA (US)

(73) Assignee: BPW Sciences, LP, King of Prussia, PA (US)

( * ) Notice: Subject to any disclaimer, the term of this patent is extended or adjusted under 35 U.S.C. 154(b) by 143 days.

(21) Appl. No.: 14/238,098

(22) PCT Filed: Aug. 3, 2012

(86) PCT No.: PCT/US2012/049530
§ 371 (c)(1),
(2), (4) Date: Mar. 10, 2014

(87) PCT Pub. No.: WO2013/022752
PCT Pub. Date: Feb. 14, 2013

(65) Prior Publication Data
US 2014/0175330 A1    Jun. 26, 2014

Related U.S. Application Data

(60) Provisional application No. 61/521,172, filed on Aug. 8, 2011.

(51) Int. Cl.
| | | |
|---|---|---|
| *A61K 31/7048* | (2006.01) | |
| *B01D 43/00* | (2006.01) | |
| *C07D 407/12* | (2006.01) | |
| *C07D 493/04* | (2006.01) | |

(52) U.S. Cl.
CPC .......... *A61K 31/7048* (2013.01); *B01D 43/00* (2013.01); *C07D 407/12* (2013.01); *C07D 493/04* (2013.01)

(58) Field of Classification Search
None
See application file for complete search history.

(56) References Cited

U.S. PATENT DOCUMENTS

| | | | |
|---|---|---|---|
| 4,627,292 A | | 12/1986 | Dekrone |
| 5,578,486 A | * | 11/1996 | Zhang .................... C12N 15/76 435/243 |
| 6,766,694 B2 | | 7/2004 | Hubschen |
| 7,896,944 B2 | * | 3/2011 | Karr ........................ C05F 11/02 423/308 |
| 2009/0208598 A1 | | 8/2009 | Novitsky et al. |
| 2011/0060132 A1 | | 3/2011 | Lewis |

OTHER PUBLICATIONS

Ghernaout et al. Electromagnetic treatment-doubled electrocoagulation of humic acid in continuous mode using response surface method for its optimisation and application on two surface waters. Desalination and Water Treatment. Oct. 2010.*
Int'l Preliminary Report on Patentability issued Feb. 20, 2014 in Int'l Application No. PCT/US2012/049530.
Albers et al. '13C-NMR Chemical Shift Databases as a Quick Tool to Evaluate Structural Models of Humic Substance' Feb. 2, 2010, abstract, p. 98, col. 2, para 1, Fig. 3 and Table 1.
PubChem compound CID 5359407 Mar. 28, 2005 (retrieved from http://pubchem.ncbi.nlm.nih.gov/summary/summary.cgi?cid=5359407 on Oct. 4, 2012, p. 1.
Ramunni et al. Use of ultrasonic treatment for extraction of humic acid with inorganic reagents from soil Org. Geochem vol. 8 p. 241-246 (1985) abstract, p. 242, col. 1, para 2; p. 242, col. 2, para 5; p. 242, col. 1, para 8 to col. 2, para 1.
International Search Report, dated Mar. 14, 2013.
Extended European Search Report issued Aug. 26, 2015 in EP Application No. 12822707.1.

* cited by examiner

*Primary Examiner* — Tanisha Diggs
(74) *Attorney, Agent, or Firm* — Panitch Schwarze Belisario & Nadel LLP

(57) ABSTRACT

Improved methods for the separation and isolation of bioactive polyelectrolytes, such as humic acid, fulvic acid, ulmic acid, and humin, from any one or a combination of naturally occurring or synthetically produced humified organic matter (HOM) are described. The methods involve the application of an electromagnetic field to an aqueous slurry of the HOM to thereby separate one or more bioactive polyelectrolyte fractions from the remaining of the HOM. Related systems and isolated bioactive polyelectrolyte fractions are also described.

5 Claims, 3 Drawing Sheets

Fig 2.1
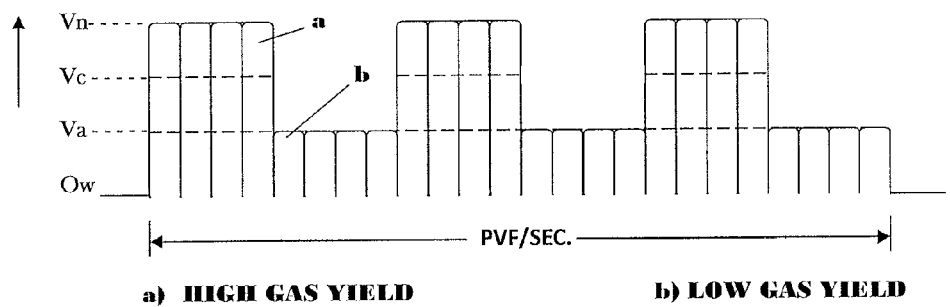
a) HIGH GAS YIELD    b) LOW GAS YIELD
Fig 2.2
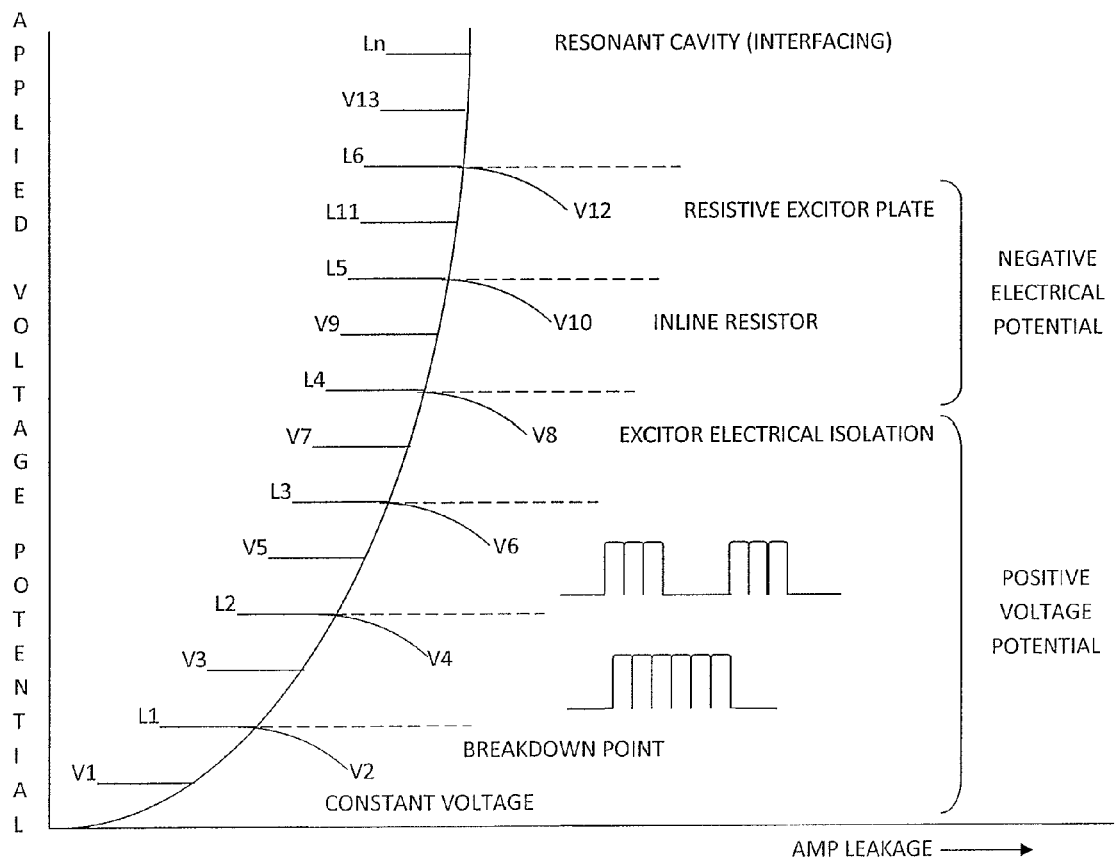

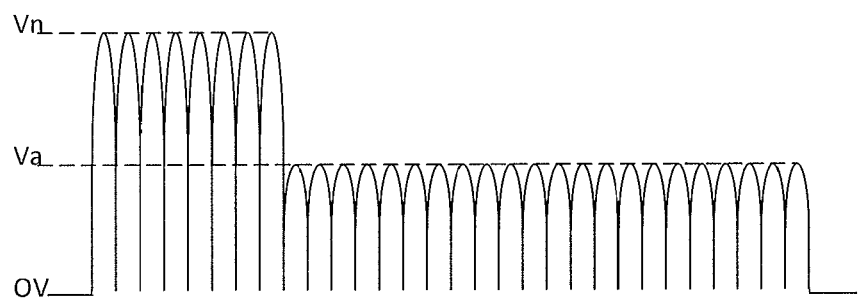
Fig 2.3
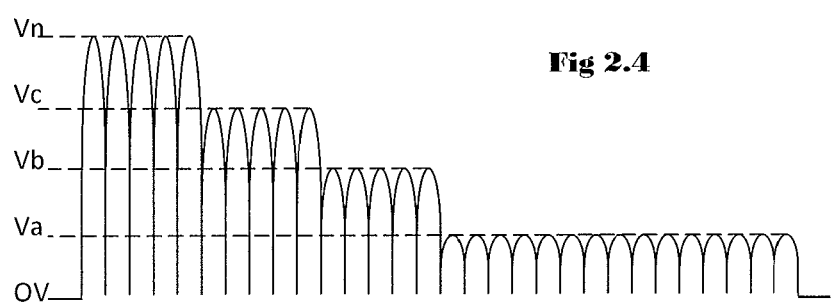
Fig 2.4
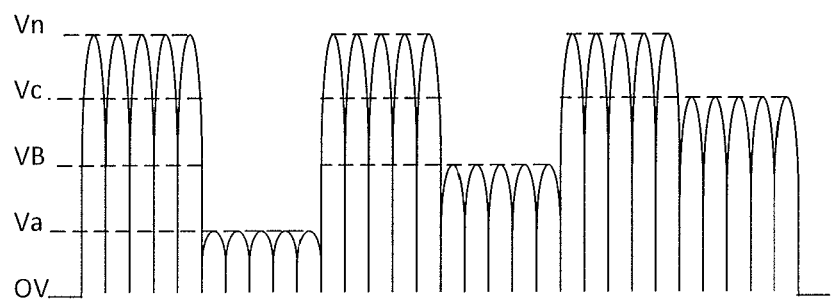
Fig 2.5

METHODS FOR EXTRACTION OF BIOACTIVE POLYELECTROLYTES FROM HUMIFIED ORGANIC MATERIALS

CROSS-REFERENCE TO RELATED APPLICATION

This application is a Section 371 of International Application No. PCT/US2012/49530, filed Aug. 3, 2012, which was published on Feb. 14, 2013, under International Publication No. WO 2013/022752 A1, and the disclosure of which is incorporated herein by reference.

BACKGROUND OF THE INVENTION

Humic substances (HS) are ubiquitous in nature and arise from the decay of plant and animal residue in the environment. HS are among the most widely distributed natural products on the surface of the earth, and are the major organic components of soil (humus), lakes, rivers and geological deposits such as peat, leonardite, lignite (brown coal) and organic clays. Humified organic material (HOM) is relatively stable, but can vary in composition based on its location, deposit type, depth and age. HOM contains a complex mixture of organic molecules, such as bioactive polyelectrolytes (BPs).

BPs include numerous bioactive, naturally occurring, related, but not identical, high-molecular-weight polymers. Examples of BPs include, but are not limited to, fractions of HS, such as humic acid (HA), fulvic acid (FA), humin or ulmic acid (UA). The differences among BPs include a considerable variation in molecular weight and size, the number of functional groups (e.g., carboxyl, phenolic HO) and the extent of polymerization that has taken place. HA and FA have received broad international attention within the scientific community due to their wide range of bioactive characteristics. See, e.g., Drozd J., 1978, Studies of chemical and physiochemical properties of humus compounds of some taxonomic soil units, *Rosprawy Naukowe, Zeszyt* 13, *AR Wroclaw* pp. 65. BPs are useful for multiple functions in humans, other animals and plants.

Extraction of a particular BP fraction of the desired molecular functionality from HOM can be challenging. Extraction processes that are largely dependent on acid/base precursor separation via ionic exchange can dramatically alter the molecular structures of BPs, thus affecting their inherent characteristics. In addition, despite extensive research directed to understanding the formation and composition of HOM, the precise chemical structure of the constituents of HOM remains unknown. HOMs that have been isolated from different sources experienced different environments, oxidative states and humification processes, thus they typically exhibit widely varying compositions. These variations result in the production of a vast and complex array of BPs that range in molecular weights from 60 to 300,000 Da and whose polymers vary in length from a few nanometers to several microns.

Alkali extraction is a widely used method for isolation of HS from solid-phase source materials, such as soils, peat, and leonardite, as recommended by the International Humic Substances Society (IHSS). In general, HS is isolated from the solid-phase source materials by alkali extraction with aqueous NaOH, followed by precipitation of humic acid at low pH and a series of desalting steps involving cation exchange, dialysis, etc. to obtain fulvic acid. Through these procedures, all organic acids that are extracted from a solid-phase source material are ultimately found in either the humic acid or fulvic acid fraction, which may require further chemical processing prior to use.

The alkali extraction process generally only recovers approximately ½ to ⅔ of the total HOM and may alter structures of BP molecules in the extract. In addition, current alkali and acid extraction methods may present other undesirable characteristics. For example, alkali dissolves protoplasmic and structural components from fresh organic tissues, which may contaminate the HOM. Also, under alkaline conditions, auto-oxidation of some organic constituents occurs as they come into contact with air, both during the extraction and when the extracts are allowed to stand. In addition, other chemical changes can occur in alkaline solutions, such as condensation between amino acids and aldehydes and quinines, etc. These undesirable extraction features found in the conventional practices in industry preclude the use of the extracted BP materials in many downstream applications.

Thus, there is a need of an improved method for the isolation of BPs from HOMs. Embodiments of the present invention relate to such an improved method as well as related devices and BPs isolated by the improved method.

BRIEF SUMMARY OF THE INVENTION

The present invention overcomes many of the problems of the prior art extraction methods, providing a method of isolating or extracting one or more BPs from HOMs with high purity but with no or very little alteration to the native BP structures. The methods afford reproducible results for the extraction of BPs from various HOM sources, including, but not limited to, lignite (brown coal), leonardite, humilite, humic substances, peat, ocean mud bottoms, organic clays, river, lake and swamp waters.

In one general aspect, the present invention relates to a method of isolating a bioactive polyelectrolyte (BP) fraction from a humified organic material (HOM), the method comprising:

providing an aqueous slurry comprising the HOM;

applying an electromagnetic field to the aqueous slurry to obtain an electromagnetic field treated HOM; and isolating the BP fraction from the electromagnetic field treated HOM.

In a preferred embodiment of the present invention, a pulsed electromagnetic field is applied to the aqueous slurry to thereby separate the BP from the remaining of the HOM.

In another general aspect, the present invention relates to a system for separating a bioactive polyelectrolyte (BP) from a humified organic material (HOM), the system comprising an electromagnetic cell and an aqueous slurry comprising the HOM placed within the electromagnetic cell, wherein the electromagnetic cell is capable of providing an electromagnetic field to the aqueous slurry to thereby separate the BP from the HOM.

Yet another general aspect of the present invention relates to an isolated bioactive polyelectrolyte (BP) produced by a method according to an embodiment of the present invention. In one embodiment of the present invention, an isolated BP fraction comprises an isolated fulvic acid fraction having a molecular weight range of 150 to 1300 dalton.

In a preferred embodiment of the present invention, the isolated BP fraction comprises an isolated fulvic acid fraction having a molecular weight range of 150 to 800 dalton.

Other aspects, features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawing embodiments which are presently preferred. It should be understood, however, that the invention is not limited to the precise arrangements and instrumentalities shown.

In the drawings:

FIGS. 2.1 to 2.5 illustrate exemplary pulsed electromagnetic signals that can be applied to the HOM slurry in the extraction methods according to embodiments of the present invention.

DETAILED DESCRIPTION OF THE INVENTION

Figure 1:
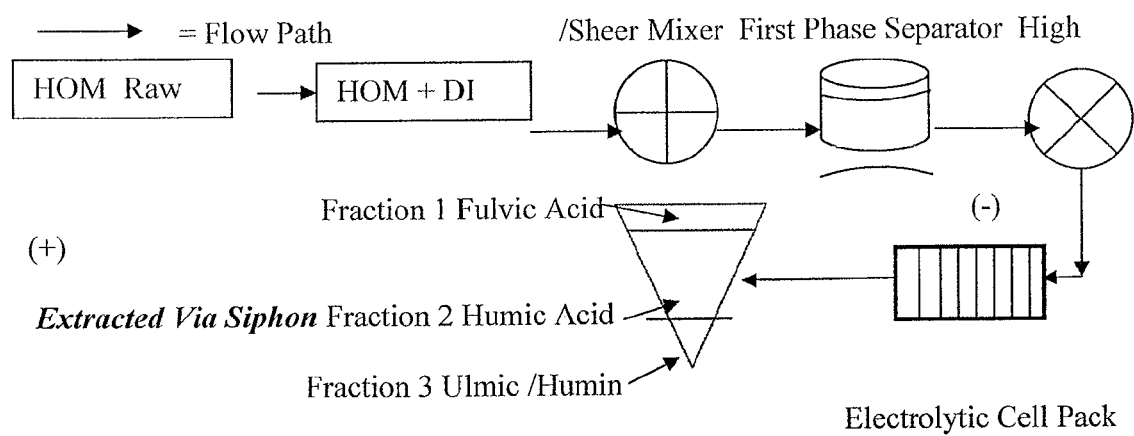
FIG. 1 illustrates a flow diagram of a BP isolation or extraction process according to an embodiment of the present invention, i.e., Black BP extraction method.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural references unless the context clearly dictates otherwise.

In one general aspect, the present invention relates to an extraction method for separating one or more bioactive molecules from any one or a combination of naturally occurring or synthetically produced HOM source materials. The bioactive molecules include, but are not limited to, bioactive polyelectrolytes (BPs) such as humic acid (HA), fulvic acid (FA), ulmic acid (UA), etc. Methods according to embodiments of the present invention can be easily implemented and provide an economical and reproducible means of separating, collecting, and extracting BPs as well as their individual components in a concentrated form with no or very little alteration of their native structures. Methods according to embodiments of the present invention can also be used to remove contaminants or undesirable ingredients from the BPs. The contaminants or undesirable ingredients include, but are not limited to, heavy metals such as chromium, mercury and lead, and metals such as iron, aluminum and silica, as well as other toxic or undesirable organic or inorganic matters.

As used herein, the term "bioactive polyelectrolyte" or "BP" refers to any bioactive polymer whose repeating units bear an electrolyte group, as well as the salts and esters of the bioactive polymer. BPs can have a wide and valuable range of beneficial uses in humans, other animals and plants. BPs can be made up of five (5) basic elements: carbon, hydrogen, nitrogen, oxygen and sulfur, while carbon and oxygen being the main components. The principal organic groups of BPs include, for example, phenolic, carboxylic, OH, aliphatic CH, carbonyl, conjugated carboxyl, aromatic $CH_2$ or $CH_3$, ionic carboxyl and possibly others. BPs can be classified and, to some extent, identified by their degree of polymerization, molecular weight and atomic particle size, characteristics that appear to be dictated by the extent and type of humification processes that produced the BPs.

Examples of BP include, but are not limited to, humic acid (HA), fulvic acid (FA), humin and ulmic acid (UA). In general, fulvic acid comprises low-molecular weight polymeric compounds, while humic acid comprises high molecular weight polymeric compounds. The humic and fulvic acid fractions of BP are a combination of colloids and nano-crystalline materials. While their exact structures are still not yet fully characterized, the HA and FA have been shown to have excellent bioactive capabilities for living matters.

As used herein, the term "humic acid" or "HA" refers to a fraction of humic substances that is not soluble in water at low pH, e.g., below about 2, but soluble at higher pH, e.g., about 6 or higher. It is insoluble in an acid solution, methyl ethyl ketone (MEK) and methyl alcohol (MA), but is soluble in an alkali solution. HA comprises a mixture or collection of different acids containing carboxyl and phenolate groups, some of which are based on a motif of aromatic nuclei with phenolic and carboxylic substitutions that are linked together. HA can have one or more of quinone, phenol, catechol and sugar moieties.

The proposed structures of HA contain free and bound phenolic OH groups, quinine structures, nitrogen and oxygen as bridge units and COOH groups placed variously on aromatic rings (Stevenson F. J., 1982, Humua Chemistry: Genesis, Composition, Reactions, John Wiley & Sons, Interscience 443 p. New York 1982). Some of the previously proposed HA structures are illustrated in Formula (I) and Formula (II) below.

Formula (I)

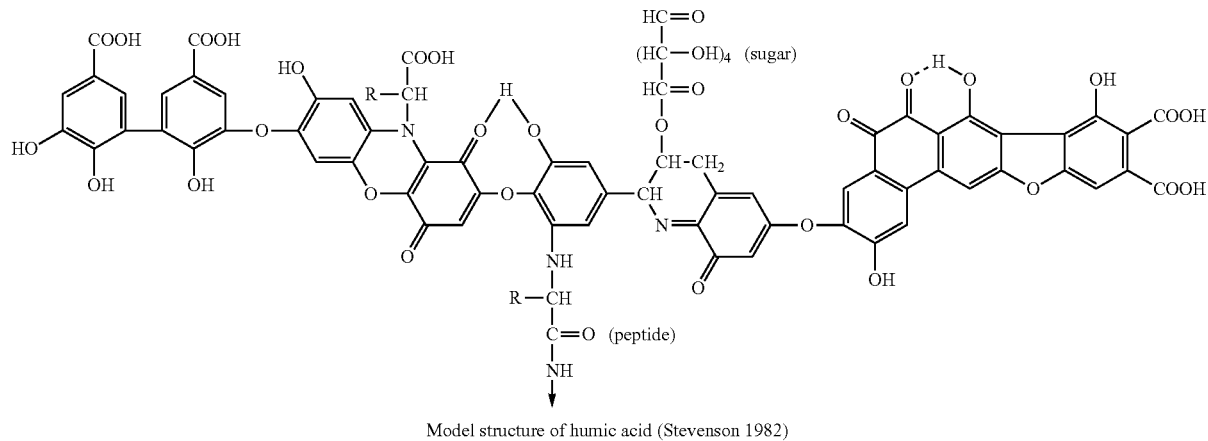

Model structure of humic acid (Stevenson 1982)

Formula (II)

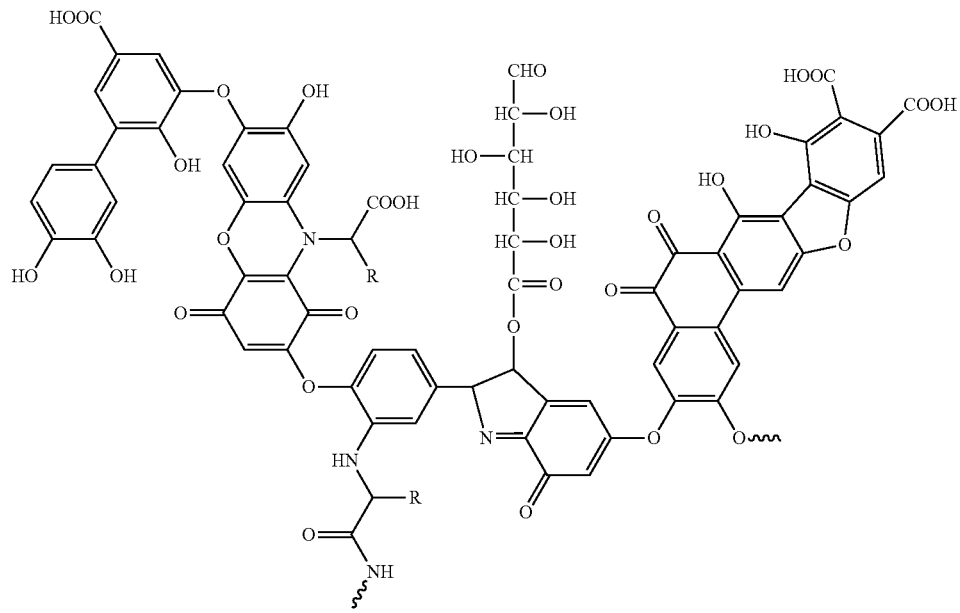

(F. J. Stevenson (1994) *Humus Chemistry: Composition, Genesis, Reactions,* John Wiley & Sons, New York, also as published in Wikipidia Free Encyclopedia, 2009).

HA behaves functionally as a dibasic acid or tribasic acid. It can form complexes with ions such as $Mg^{2+}$, $Ca^{2+}$, $Fe^{2+}$ and $Fe^{3+}$. As used herein, the term "HA" encompasses the esters, salts or ion complexes of humic acid. When the cation exchange sites on HA molecules are filled predominately with an element other than hydrogen, the HA molecules are called humates. In general, humates of a monovalent inorganic or ammonium ionic nature are stable in water, but humates of a multivalent cation nature are unstable.

As used herein, the term "fulvic acid" or "FA" refers to a fraction of humic substances that is soluble in water under all pH conditions. It is also soluble in MEK, MA and acids. It generally has a yellow (fulvus) to yellow-brown color. FA comprises a mixture or collection of different acids containing carboxyl and phenolate groups.

The proposed structure of FA contains both aromatic and aliphatic structures that are extensively substituted with oxygen-containing functional groups. A previously proposed FA structure is illustrated in Formula (III), see Buffle J., Greter F. L., Haerdi W., 1977, Measurements of Complexation Properties of Humic and Fulvic Acids in Natural Water, With Lead & Copper Ion-Selective Electrodes. *Anal. Chem.* 49: 216-222:

Formula (III)

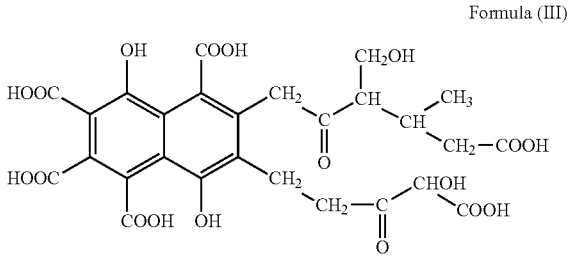

Model structure of fulvic acid by Buffle

As used herein, the term "FA" encompasses the esters, salts or ion complexes of fulvic acid.

As used herein, the term "ulmic acid" or "UA" refers to a fraction of humic substances that is soluble in alkali and methyl ketone, but is insoluble in methyl alcohol. The term "UA" encompasses a mixture or collection of high molecular weight polymers, including the esters, salts or ion complexes of ulmic acid.

As used herein, the term "humin" refers to a fraction of humic substances that is insoluble in water at all pH. The term "humin" encompasses a mixture or collection of high molecular weight polymers, including the ester or salt forms of the polymers.

As used herein, an "isolated BP fraction" is substantially free of the non-BP substances present in the source where the BP fraction is isolated. An isolated BP fraction can be an isolated fraction of humic substances, such as an isolated FA fraction that is substantially free of the non-FA substances present in the source where the FA is isolated, an isolated HA fraction that is substantially free of the non-HA substances present in the source where the HA is isolated, etc. An isolated BP fraction can also contain two or more isolated fractions of humic substances, such as two or more of UA, HA, FA and humin fractions, that is substantially free of the other substances. A BP fraction is "substantially free of" the non-BP substances when there is less than about 30%, 20%, 10%, or 5% or less, and preferably less than 1%, by dry weight, of the non-BP substances (also referred to herein as "contaminating substances" which may include such substances as heavy metals of, arsenic, lead, chromium, mercury and so on to name only a few as examples).

In one general aspect, embodiments of the present invention relate to an improved method of obtaining an isolated BP fraction from an HOM. The method comprises providing an aqueous slurry comprising the HOM, applying an electromagnetic field to the aqueous slurry to obtain an electromagnetic field treated HOM in which BP fraction is separated from the remaining of the HOM, and isolating the BP fraction from the electromagnetic field treated HOM. Preferably, the electromagnetic field comprises a pulsed electromagnetic signal.

While not wishing to be bound by theories, it is believed that the applied electromagnetic signal closely matches the natural atomic frequency or molecular energy of individual BP in the HOM, creates molecular harmonics with the BP, thereby assisting in the separation of the BP. For example, the applied electromagnetic signal may assist the separation by changing the molecular interactions within HOM, e.g., by breaking hydrogen or other bonds or interactions between the molecules thus allowing separation of the molecules.

According to embodiments of the present invention, BPs can be isolated from any HOM source material including, but not limited to, lignite (brown coal), leonardite, humilite, organic clays, soil (humus), peat, lakes/rivers, other HOM sources known to exist in natural geological formations, or that can be produced by known methods from organic biowaste materials, such as agricultural, animal and human materials, by various refining processes.

One or more BP fractions have been isolated using a method according to an embodiment of the present invention, e.g., a Black BP extraction method, which is illustrated in the flow diagram of FIG. 1 and described below. It is to be noted, however, that this description of these specific embodiments is merely illustrative of the principles underlying the inventive concept. Various modifications of the disclosed embodiments will, without departing from the spirit and scope of the invention, be apparent to persons skilled in the art.

When the HOM source material is a liquid, such as lake or river water, the liquid is preferably concentrated before applying the electromagnetic field to it.

When the HOM source material is a solid, such as lignite (brown coal), leonardite, humilite, organic clays, soil (humus), peat, the solid is preferably first subject to agglomeration reduction by one or more methods known in the art. For example, sonic reduction, blast reduction and other processes can be used to size the HOM source materials to a granular size, preferably not greater than 0.25 thousandths of a meter in diameter, while simultaneously removing foreign matter in the source materials. Preferably, the process selected should not be of a crushing, grinding or overly abrasive nature, so as not to crush, grind or abrade foreign matter in the HOM, which is not desired in the finished product. The foreign matter includes, for example, minerals and metals manifesting themselves in clays, rocks, stones, etc.

HOM is generally of a softer nature than that of the inorganic materials sometimes occurring throughout the HOM geology or source materials. Preferably, the much harder inorganic rocks, stones, metal agglomerates and other hard particles occurring in the HOM geology are first removed using methods known in the art in view of the present disclosure, such as by sedimentation, centrifugation, etc.

After the removal of inorganic rocks, stones, metal agglomerates, etc., the HOM source material can then be placed in a container, such as a stainless steel, high density non-reactive plastic or glass lined vessel. Deionized (DI) water is added to the HOM raw material in sufficient amounts to provide an aqueous slurry, generally in a ratio of from about 200 to about 1,000 grams of HOM raw material in about 1-3 gallon of DI water. The aqueous slurry is mixed for a period of time until all HOM material is completely wetted, thereafter allowing the HOM/DI water slurry to stand for a period of time sufficient to allow the HOM material to soften in preparation for further processing such as, but not limited to, grinding, milling, filtration and separation.

After the selected soak time has been attained, the HOM/DI water slurry is preferably processed further using one of a number of particle reduction devices capable of handling slurry materials, such as the commercially available lightening mixers, ball mills, jet mills, high speed shears and other means known within the industry. The slurry/particle reduction methodology reduces the HOM particles so that they will pass through a 200 mesh screen, and, more desirably, through a 300 mesh screen, resulting in final particle sizes ranging from 300 mesh down to nano-sized dust. The time needed to accomplish the desirable particle sizes will depend on the reduction method chosen. Additional polymerization and cross linkage may occur in HOM when exposed to heat and/or pressure that are generated by or associated with the particle reduction method. Thus, it is desirous to choose a method that is a one-pass-through reduction method, as opposed to a longer term grinding method, so as to cause little or no alteration to molecular structures of BPs in the HOM.

Upon completion of the HOM particle size reduction, the slurry is allowed to relax for a time period ranging from 4-24 hours, preferably 24 hours. Then, the HOM slurry is exposed to a high speed jet mill for further particle reduction. A jet mill is capable of reducing the sizes of solids in the slurry, e.g., from 5 to 10 microns down to nanometer sizes.

An electromagnetic field provided by a DC power source is then applied to the HOM sol or slurry to separate the bioactive polyelectrolytes within the HOM sol. The DC power source contains at least one anode and one cathode source (plate). The anode receives and disburses positive electrons while the cathode receives and dispenses negative electrons, thereby setting up an electromagnetic cell, to which the HOM sol is passed or contained. The sol in the electromagnetic cell can be exposed to a variety of electromagnetic signals with varying wavelengths, which assist the separation of BPs in the HOM. Similar to any electrophoretic or electrophoresis method, the separation of BPs involves the movement of charged molecules under the influence of electric fields.

In a method according to an embodiment of the present invention, any electromagnetic field can be utilized. Preferably, a method according to an embodiment of the present invention uses a pulsed electromagnetic signal, which can be provided by means known in the art in view of the present disclosure. For example, the pulsed electromagnetic signal can be generated by a modulating, pulsed DC power signal via a toroidal transformer and bridge rectifier. Examples of the pulsed electromagnetic signals that can be used in the present invention include, but are not limited to, those depicted in FIGS. 2.1 to 2.5.

FIG. 2.1 depicts a preferred electromagnetic signal used in the present invention, showing the applied frequency and time sequence per second. This depiction is read directly from an acelescope for voltage, amperage and cycles (Hz). The letter designations appearing to the right side of the wave curve indicate action items, such as, OV=start of voltage input, Va=first low frequency cut off point, Vb=midrange of high frequency wave, Ve=point of which hydrogen and oxygen gas is being generated due to the electrolytic effect of the water disassociation of the SOL, and Vn=the cut off point for the high frequency signal. Low (b) and high (a) gas yields are noted as indications of the efficiency of the electromagnetic signal and the SOL electrical conductance, both of which are design features of this extraction process.

FIG. 2.2 depicts the physics and electrical design parameters of one means of obtaining the resonance cavity (capacitance cavity) through which the liquid SOL flows during separation conditioning, and a diagram profile of the electromagnetic signal, frequency, positive and negative voltage application points at which the resonance is created within the cavity. The codes (ref alpha numeric titles) are explained with the side notes. For example:

V1=constant input voltage
V2=Breakdown of the Capacitance Resistance Point
V7=Cut in of electrical isolator exciter in the system
V9=Inline resistor activation point in the system
V13=Resonant cavity charge state point interfaces
V3 to V6, V8, and V10 to V12, indicate transitional positions occurring between defined plateaus in the electromagnetic signal profile, thus are not individually defined farther.

Key positions in the electromagnetic signal, at which certain events occur, are indicated in FIG. 2.2. This is only an illustration of one way of creating a high/low resonance electromagnetic signal able to be modulated from 1,500 Hz up to 150,000 Hz.

Other methods known to those skilled in the arts can be used as means to accomplish the desired electromagnetic signals necessary to effect separation of the BP fractions in view of the present disclosure. For example, FIGS. 2.3 thorough 2.5 illustrate other alternate resonance frequencies that can be used to aid in the separation of BPs in the HOM SOL.

In one embodiment of the present invention, the electrolytic process uses a DC electrical signal of about 1.4 to about 3.4 volts per square inch of cell surface area, at an amperage of about 0.24 amp to about 2.8 amps per square inch of cell surface area. The cell contains 1 anode and 1 cathode plate with a space in between of a calculated distance.

In one embodiment, the resonance (modulations of the chosen signal) or the signal is modulated from 0-16,000 Hz. In another embodiment, the signal is modulated from 0 to 120,000 Hz. In a preferred embodiment, the resonance is about 16,000 to about 65,000 Hz.

The Hz cycles can be chosen to provide a specific range of cycles, such as those illustrated in FIGS. 2.1 through 2.5. For example, FIG. 2.3 illustrates a 16,500 Hz to 41,000 Hz signal. FIG. 2.4 illustrates a signal of 8,000 to 16,000 Hz, then 22,000 Hz and finally to 41,000 Hz in a complete cycle.

The electromagnetic field, such as the pulsed electrophoretic signal, separates the various fractions of HOM, such as the humic acid, fulvic acid, ulmic acid, and humin by molecular selection, based on the particular molecular size, weight, charge and structure of BPs. By adjusting the electromagnetic signal to which the HOM slurry is exposed to, separation of selective BPs within HOMs is made possible. BP factions that have not been produced by the conventional methods can be prepared reproducibly by methods according to embodiments of the present invention.

In one embodiment of the present invention, using a method according to an embodiment of the present invention, an FA fraction consisting of molecules that range in molecular weight from about 185 to about 800 Da, an HA fraction from about 5,000 to about 50,000 Da, and an UA fraction from about 20,000 to about 90,000 Da were separated and extracted from HOMs.

In view of the present disclosure, those skilled in the art would readily appreciate that more finite fractions of BPs can be separated by methods according to embodiments of the present invention, for example, by varying the electrophoretic signal applied to the HOM.

According to an embodiment of the present invention, the separated BPs can be collected and subject to further separation for individual BP or subgroups or subcomponents of BPs. The separated BPs can also be subject to further separation for enhanced purity.

A method according to an embodiment of the present invention also allows for the separation of unwanted elements within the HOM source material from the desired BPs. Depending on the source, the HOM may contain dissolved or suspended elements or ingredients that are not useful or even deleterious to the downstream application intended for the extracted BPs. The undesirable elements or ingredients may include, for example, heavy metals, chromium, mercury, lead, antimony, etc., common metals such as iron, aluminum, silica, or other organic or inorganic matters. Because the method according to embodiments of the present invention is electrolytic in nature, the unwanted elements or ingredients can be separated from the BPs by modifying the electrical signal being used in the electromagnetic field, using electrophoretic methodologies known to those skilled in the art in view of the present disclosure.

The unwanted elements or ingredients can be removed from the separated BPs in one step during the separation of the BPs. They can also be removed from the separated BPs in separate steps, either before or after the desired BPs are isolated from the HOM.

According to embodiments of the present invention, after one or more rounds of separation of the BPs from the HOM, the remaining of the HOM can be subject to one or more rounds of separation by repeating the steps of the separation methods to extract additional BPs in the HOM. The separation can be automated and continuous.

The separated BP fraction can be collected by various methods known in the art in view of the present disclosure.

In one embodiment of the present invention, the BP fraction is collected as the solid precipitant on the cathode source of the electrophoretic device, e.g., the plate of the electrolyzer cell. This is accomplished by controlling the length of time of the sol staying in the electromagnetic cavity of the electrolyzer, the temperature, voltage and current of the electrolytic cavity and the solid content of the sol as it enters the electrolyzer cell.

In another embodiment of the present invention, after being treated with the electromagnetic field, the electro magnetized HOM sol is passed into a settling or fractionation column commonly known and used for these purposes, where the electrolyzed BPs in the sol separates due to electromagnetic repulsion based on species molecular weight, size, charge and structure. The fractionation column is allowed to stand and settle for an appropriate time, e.g., from about 10 minutes to about 24 hours, preferably 6-8 hours, to allow fractionation/separation of the sol constituents, thereafter allowing the one or more separated BP fractions to be collected by convenient methods used in the industry for equipment of this type in view of the present disclosure.

In yet another embodiment of the present invention, filtration can be used to collect the separated BP fraction. Many known filtration separation methods can be used in the present invention in view of the present disclosure. Based on the definitive molecular weight and inherent particle sizes of the BP fraction, a progressive filtration system can be employed successfully in a method according to an embodiment of the present invention, whereby a series of micro, macro and nano size filtration columns are employed to collect and separate BP fractions, such as ulmic acid, humic acid and fulvic acid.

According to an embodiment of the present invention, a pulsed electromagnetic energy is provided to an HOM slurry via a bridge rectifier into a cathode and anode cell that imparts the selected electromagnetic field into and through the HOM slurry. After a select length of exposure to the electromagnetic energy, the slurry is separated by a first filtration system using one of numerous well-known methods in the industry for slurry liquid/particle separation. For example, a vacuum three tier chambered sieve consisting of a stage 1 (internal) layer of 200 mesh size sieves, a stage 2 (intermediate) layer of 300 mesh size sieves and a stage 3 (final) layer of 400 mesh size sieves, can be used for the first filtration. The HOM slurry is run through these sieve separators and the liquid supernatant (sol) is collected in a container made of glass or a similarly non-reactive material. The solid remaining on the filters is collected and washed with DI water and allowed to stand/soak for an additional 24 hours, after which it is subject to the treatment of the pulsed electromagnetic energy and other aforementioned steps. This is a working cycle designed to extract the remaining residual BPs from the HOM. These steps can be repeated as necessary until the sol is pale yellow, indicating that the organic media has been removed. Then, the remaining solid on the filters is disposed of.

The various liquid supernatants (sols) are combined and allowed to stand in a vessel that is designed or convenient for column separation of layered materials, where the sols are either allowed to separate by molecular weight, thereafter collecting the fractions by commonly known methods, or by molecular sieves, distillation or other methods known to those skilled in the art in view of the present disclosure.

Another general aspect of the present invention relates to a system for separating at least one bioactive polyelectrolyte (BP) from a humified organic material (HOM). The system comprises an electromagnetic cell capable of providing an electromagnetic field to an aqueous slurry comprising the HOM to thereby separate the at least one BP from the remaining of the HOM.

In one embodiment, the system comprises an electromagnetic cell that is capable of providing a direct-current of about 1.4 volts to about 3.4 volts per square inch of cell area, at about 0.24 amp to about 2.8 amps per square inch of the cell surface area, and a signal resonance of about 0 Hz to about 120,000 Hz, preferably 20,000 to about 65,000 Hz.

In another embodiment, the system further comprises one or more devices for collecting the separated at least one BP, such as a column or a filtration subsystem for collecting the separated at least one BP.

Using an extraction method according to an embodiment of the present invention, a specific BP having a desirable structure and property can be reproducibly isolated, not only from the same HOM but also from HOM raw materials of different sources by tuning the parameters of the electromagnetic field applied to the HOM. BPs prepared by a method according to an embodiment of the present invention can be different from that prepared by the prior art method, even though the same HOM source material is used. Accordingly, another general aspect of the present invention relates to an isolated bioactive polyelectrolyte (BP) produced by a method according to an embodiment of the present invention.

Using a method according to an embodiment of the present invention, various BP fractions can be isolated, e.g., by varying the electrophoretic signal applied to the HOM.

In one embodiment of the present invention, an isolated BP fraction comprises at least one of an isolated ulmic acid fraction having a molecular weight range of about 50,000 to about 160,000 dalton; an isolated humic acid fraction having a molecular weight range of about 3,000 to about 50,000 dalton; and an isolated fulvic acid fraction having a molecular weight range of about 150 to about 1,300 dalton.

It was reported that the most effective BP materials have a molecular weight in the range of about 100 to about 1000 Da, with the most active BP materials being around 100 to 800 Da. An HA fraction prepared by a method of an embodiment of the present method falls within that of the most active BP materials.

Table 1 compared the molecular weights of the HA and FA extracted by a method according to an embodiment of the present invention with the respective fractions prepared by a conventional alkali extraction method, IHSS method.

TABLE 1

| Molecular Weight Comparison | | |
|---|---|---|
| | Black BP Method | IHSS Method |
| Humic Acid | 5,000 to 50,000 | 8,000 to 75,000 |
| Fulvic Acid | 150 to 800 | 250 to 2,200 |

In one embodiment of the present invention, the isolated BP fraction comprises an HA fraction having an average molecular weight of 5,000 or more to 50,000 or less dalton.

In another embodiment of the present invention, the isolated BP fraction comprises an FA fraction having an average molecular weight of about 150 or more to 2,000 or less dalton, preferably about 500 or more to 1,000 or less Da, and more preferably about 150 or more to 800 or less Da.

FAs according to embodiments of the present invention have sufficiently lower molecular weights and allows more specific chemical structure modeling compared to those in the prior art that have ill defined macromolecular shapes. According to an embodiment of the present invention, an FA is prepared using an electromagnetic signal profile as that illustrated in FIG. 2.5, with an input voltage at 2.4 V and amperage of 1.0 amp per square inch of cell surface area, at a pH of the SOL at 4.0. Based on quantitative characterization of the FA fraction resulting from two-stage normal-phase chromatography of Selected Raw material Fulvic Acid base (SRFA), the FA has Formula (IV):

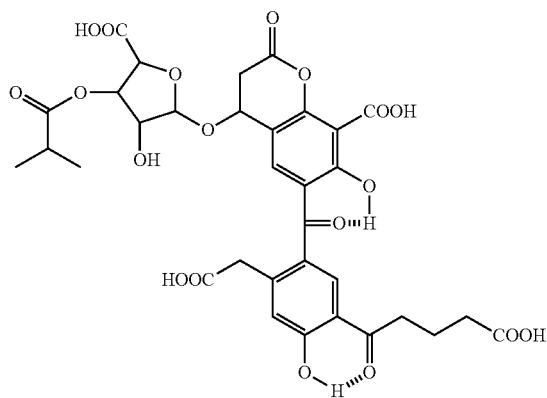

Formula (IV)

The FA according to Formula (IV) is enriched in ring structures, both aliphatic and aromatic, and has an average of four carboxylic acid groups per molecule. This is different from that described in the prior art, such as Formula (III) described above.

In another embodiment of the present invention, the isolated FA fraction has an average molecule weight of 951 Da as measured by vapor pressure osmometry. The FA fraction contained 9.1 milliequivalent (mEq) COOH, 3.3 meq phenolic OH, 3.6 meq alcoholic OH and 3.1 meq C=O per gram of the FA. The elemental analysis (in %) showed that the FA fraction contained 50.90% C, 44.75% O, 3.35% H, 0.75% N and 0.25% S as measured by enhanced research Ft IR spectrometer on high sensitivity analysis mode, using a Thermo Fisher Scientific model Nicolet 6700 Spectrometer. Based on the molecular data calculation, the predicted formula for the extracted FA fraction extracted by a Black BP method is $C_{28}H_{16}(COOH)_9(OH)_7(CO)_3$ In yet another embodiment of the present invention, the isolated FA fraction has a formula (V):

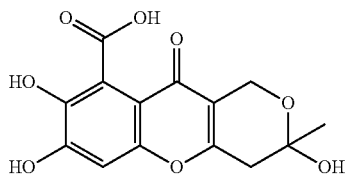

Formula (V)

An HA/FA combined sol, at first glance, appears to be colloidal in nature, i.e., microscopically dispersed evenly throughout the sol. However, if separated into its component fractions, the SOL is comprised of colloidal particles, nano-crystalline particles and nano-crystalline ionic particles. When the HA and FA fractions are separated by a conventional acid/alkaline method, there is some cross contamination or pollution of the fractions. The FA fraction still appears to be colloidal in nature because enough of the humic acid molecules remain in the principally fulvic fraction. However, when extracted by a method according to an embodiment of the present invention, the increased purity of each of the HA and FA fractions allows more accurate display of the nature of the fractions, i.e., HA is colloidal in nature and FA is ionic nano-crystalline in nature.

Humic acid fractions extracted by a method according to an embodiment of the present invention are true colloidal, they do not dissolve in water, remaining as electrically suspended molecules, or clusters of molecules. The HA fraction contains HA particles having an average particle size of about 1 to 10 microns.

Fulvic acid fractions extracted by a method according to an embodiment of the present invention are true solutions, i.e., a highly electrically charged ionic, nano-crystalline solution containing FA molecules about 1 to several angstroms in size.

According to another embodiment of the present invention, the isolated humic acid and/or fulvic acid fractions have excellent bioactive capabilities for living matters, and have a cation exchange capacity of about 200 to 800 milliequevalents per 100 grams at a pH of 7.

This invention will be better understood by reference to the non-limiting example that follows, but those skilled in the art will readily appreciate that the example is only illustrative of the invention as described more fully in the claims which follow thereafter.

EXAMPLE

HOM leonardite sample was purchased from Luscar Coal Company (Alberta, Canada). BP fractions, such as HA and FA, within the HOM leonardite sample were extracted using the Black BP method as that described above. A desirable HA fraction having a theoretical structure of Formula (II) (see above) was extracted from the HOM sample by adjusting or tuning the electromagnetic signal to match the desirable HA fraction and the incoming HOM source material, i.e., Luscar leonardite. The isolated BP fractions were examined by chromatography and other analyses, and compared with the fractions prepared by the conventional alkali extraction method.

In particular, by using an electromagnetic signal as that illustrated in FIGS. 2.1, at 1.9 V and 0.95 amps per square inch of cell surface area and the modulation cycle of 0-16,000 Hz to 41,000 Hz to 0 again, an HA fraction having the theoretical structure of Formula (II) was extracted from the Luscar leonardite HOM source material. Consistent with the data provided by Luscar Coal for the Black Earth HOM, the same HOM source material, the HA isolated by the Black BP method displayed the following components or moieties: mono-, di-, and tri-hydroxy acids, fatty acids, dicarboxylic acids, linear alcohols, phenolic acids and terpenoids. This demonstrates that a method of the present invention could indeed be used to isolate a desired BP.

Table 2 compared an FA fraction extracted by the Black BP method with that prepared by the conventional method. The technical data were either determined experimentally from the FA fraction isolated by the Black BP method or based on information provided by Luscar Coal Company.

TABLE 2

Comparison of the FA fraction prepared by different methods

|  | Black-EMP Method | Conventional Method |
| --- | --- | --- |
| C % | 40.1 | 42.26 |
| H % | 3.57 | 3.16 |
| N % | 0.67 | 1.33 |
| S % | 0.65 | 3.05 |
| O % | 55.0 | 50.2 |
| Formula | $C_{35}H_{38}N_1S_{03}O_{36}$ | $C_{37}H_{33}N_1S_1O_{33}$ |
| Carboxylic Groups | 6 | 6 |
| Phenolic Groups | 3 | 4 |
| $(Mw)^a$ (g mol$^{-1}$) | 1,058 | 1,051 |
| Cation Exchange Capacity (mg/100 gm@pH 7) | 300 to 600 | 200 to 500 |

Results in Table 2 showed that methods according to the present invention can be used to obtain BP fractions similar, but not identical, to that obtained by other extraction methods (such as the acid/base extraction methods commonly used for these purposes) using the same raw materials. By tuning the parameters of the electromagnetic field applied to the HOM, BP fractions of more specific structure and property can be reproducibly isolated.

In addition, there was also a fraction with a molecular weight of from 285 to 360 Da. This product had a formula of $C_7H_6O_4$ and appeared to be dihydroxybenzoic acid.

This is further proof that humic substances (HSs) are not estequiometric chemical species but macromolecular colloidal phases composed of fulvic fractions, humic fraction, humin fractions, and yet to be identified additional fractions. The principle organic groups are phenolic, carboxylic, OH, aliphatic CH, carbonyl, conjugated carboxyl or aromatic $CH_2$ or $CH_3$, or ionic carboxyl and possibly others.

Results of this Example illustrate that methods according to an embodiment of the present invention can be used effectively to isolate various BP fractions with desirable properties from a HOM source material.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method of isolating a bioactive polyelectrolyte (BP) fraction from a humified organic material (HOM), wherein the isolated BP fraction comprises an isolated fulvic acid fraction, the method comprising:
    providing an aqueous slurry comprising the HOM;
    applying an electromagnetic field comprising a pulsed electromagnetic field to an electromagnetic cell containing the aqueous slurry at 1.4 volts to 3.4 volts and 0.24 amp to 2.8 amps per square inch of the surface area of the electromagnetic cell, with a signal resonance of from 0 Hz to about 120,000 Hz to obtain an electromagnetic field treated HOM; and
    isolating the fulvic acid fraction from the electromagnetic field treated HOM.

2. The method of claim 1, comprising applying the electromagnetic field treated HOM to a column or filtration system to thereby isolate the fulvic acid fraction.

3. The method of claim 1, further comprising applying a second electromagnetic field to the isolated fulvic acid fraction to obtain a second isolated fulvic acid fraction.

4. The method of claim 1, wherein the electromagnetic field is provided by a toroidal transformer and a bridge rectifier.

5. The method of claim 1, wherein the electromagnetic field is applied to the electromagnetic cell at 2 volts and 1 amp per square inch of the surface area.

* * * * *